US010413368B2

(12) United States Patent
Nilsagard et al.

(10) Patent No.: US 10,413,368 B2
(45) Date of Patent: Sep. 17, 2019

(54) ARRANGEMENT FOR MINIMAL INVASIVE INTERVENTION

(71) Applicant: G-coder Systems AB, Vastra Frolunda (SE)

(72) Inventors: Jonas Nilsagard, Gothenburg (SE); Olle Takman, Molnlycke (SE)

(73) Assignee: G-coder Systems AB, Västra Frölunda (SE)

( * ) Notice: Subject to any disclaimer, the term of this patent is extended or adjusted under 35 U.S.C. 154(b) by 238 days.

(21) Appl. No.: 15/502,383

(22) PCT Filed: Aug. 18, 2014

(86) PCT No.: PCT/EP2014/067570
§ 371 (c)(1),
(2) Date: Feb. 7, 2017

(87) PCT Pub. No.: WO2160/026511
PCT Pub. Date: Feb. 25, 2016

(65) Prior Publication Data
US 2017/0224424 A1   Aug. 10, 2017

(51) Int. Cl.
*A61B 34/20* (2016.01)
*A61B 17/34* (2006.01)
(Continued)

(52) U.S. Cl.
CPC ............ *A61B 34/20* (2016.02); *A61B 1/3132* (2013.01); *A61B 17/3403* (2013.01);
(Continued)

(58) Field of Classification Search
CPC ......... A61B 34/20; A61B 90/06; A61B 90/13; A61B 90/50; A61B 2034/2055;
(Continued)

(56) References Cited

U.S. PATENT DOCUMENTS

| 5,767,839 A | 6/1998 | Rosenberg |
| 2007/0135803 A1 | 6/2007 | Belson |

(Continued)

FOREIGN PATENT DOCUMENTS

| EP | 2 147 630 A2 | 1/2010 |
| EP | 2 478 855 A1 | 7/2012 |

(Continued)

OTHER PUBLICATIONS

International Search Report and Written Opinion for corresponding International Application No. PCT/EP2014/067570 dated Jan. 30, 2015.

*Primary Examiner* — Katrina M Stransky
(74) *Attorney, Agent, or Firm* — Renner, Otto, Boisselle & Sklar, LLP

(57) ABSTRACT

The present disclosure relates to an arrangement (21, 71) for minimal invasive intervention, the arrangement (21, 71) comprising a rotation body (23, 73), a retaining device (25, 75) and at least one position sensor (27, 77, 79). The rotation body is adapted to receive a medical instrument (3, 5, 7, 9, 33), or the rotation body forms a part of a medical instrument (83). The medical instrument comprises a shaft (31, 81). At least a portion of a surface of the rotation body comprises a pattern (35, 87, 91). The retaining device is adapted to at least partly surround the rotation body, such that the rotation body is retained by the retaining device in a manner allowing rotational movement of the rotation body in relation to the retaining device. The at least one position sensor is adapted for determining a position in at least two coordinates of the pattern of the rotation body. The at least one position sensor is located at, in or on the retaining device. The disclosure further relates to a medical instrument (3, 5, 7, 9, 33, 83), a kit (63) comprising the arrangement, a system (65) for follow-up of a minimal invasive intervention and a method
(Continued)

for determining a position of a medical instrument by means of the arrangement or kit.

19 Claims, 9 Drawing Sheets

(51) Int. Cl.
    *A61B 90/00* (2016.01)
    *A61B 90/50* (2016.01)
    *A61B 90/13* (2016.01)
    *A61B 1/313* (2006.01)

(52) U.S. Cl.
    CPC .......... *A61B 17/3423* (2013.01); *A61B 90/06* (2016.02); *A61B 90/13* (2016.02); *A61B 90/50* (2016.02); *A61B 2034/207* (2016.02); *A61B 2034/2055* (2016.02); *A61B 2034/2065* (2016.02); *A61B 2090/062* (2016.02); *A61B 2090/067* (2016.02); *A61B 2090/3937* (2016.02); *A61B 2560/0233* (2013.01)

(58) Field of Classification Search
    CPC ...... A61B 2034/2065; A61B 2034/207; A61B 2090/062; A61B 2090/067; A61B 2090/3937; A61B 17/3415; A61B 17/3403; A61B 17/3423
    See application file for complete search history.

(56) References Cited

U.S. PATENT DOCUMENTS

| | | | | |
|---|---|---|---|---|
| 2010/0168763 | A1* | 7/2010 | Zhao | A61B 34/30 606/130 |
| 2013/0066192 | A1* | 3/2013 | Sarvestani | A61B 17/3403 600/424 |
| 2014/0194732 | A1* | 7/2014 | Nakaguchi | A61B 5/064 600/424 |

FOREIGN PATENT DOCUMENTS

| | | |
|---|---|---|
| EP | 2 878 325 A1 | 6/2015 |
| WO | 2014/057853 A1 | 4/2014 |

\* cited by examiner

ARRANGEMENT FOR MINIMAL INVASIVE INTERVENTION

This application is a national phase of International Application No. PCT/EP2014/067570 filed Aug. 18, 2014 and published in the English language.

TECHNICAL FIELD

The present disclosure relates to an arrangement for minimal invasive intervention. The disclosure further relates to a medical instrument, a kit comprising such an arrangement, a system for follow-up of a minimal invasive intervention and a method for determining a position of a medical instrument by means of such an arrangement.

BACKGROUND

Minimal invasive surgery aims to reduce tissue trauma, bleeding and to improve the healing process. Such surgery is performed through tiny incisions in the skin, often only a few millimeters, through which medical instruments are inserted. A miniature camera attached to a light tube, i.e. an endoscope, may be inserted through one of the incisions to provide the surgeon of a view of the operation. The surgeon may then explore what is wrong, remove unwanted objects or body parts or repair what is inside the body etc. An example is laparoscopic surgery, which may be performed in the abdomen. Minimal invasive surgery may be performed on a body of a human being or an animal.

In order to train surgeons or veterinarians before operating on a living being, interventions may be performed on a corpse of a dead human being or animal. It is also feasible to train surgeons or veterinarians utilizing training material, e.g. models made of rubber or plastic, as e.g. disclosed in patent document US 2005/0142525 A1 by Cotin et al. Training may also be performed by simulation in virtual reality, as e.g. disclosed in patent document U.S. Pat. No. 8,007,282 B2 disclosing a medical simulation interface apparatus.

As part of the training, it may be of interest to track the movements of the instrument utilized inside the body. In the medical simulation interface apparatus disclosed by U.S. Pat. No. 8,007,282 B2, it is, for example, possible to track movements of the instruments by means of a plurality of mechanical interfaces.

However a difference between training, being in virtual reality or with model materials, and real world minimal invasive surgery, is the hygienic demands applicable when operating on living beings. There is then often a desire to be able to sterilize or clean the objects and medical instruments. Therefore arrangements used for tracking movements of instruments in prior art training apparatuses, as in U.S. Pat. No. 8,007,282 B2, have been found to be unsuitable for use in real world minimal invasive surgery.

Although the training apparatuses become better and better, there is still a step between training and real world minimal invasive surgery.

SUMMARY

The object of the present disclosure is to overcome or ameliorate at least one of the disadvantages of the prior art, or to provide a useful alternative.

The object above may be achieved by the subject-matter of claim 1. Embodiments are set forth in the appended dependent claims, in the following description and in the drawings.

Thus, in a first aspect of the present invention there is provided an arrangement for minimal invasive intervention, the arrangement comprising a rotation body, a retaining device and at least one position sensor. The rotation body is adapted to receive a medical instrument adapted for minimal invasive intervention, or, as an alternative or a complement, the rotation body itself forms a part of a medical instrument. The medical instrument comprises a shaft. At least a portion of a surface of the rotation body comprises a pattern. The retaining device is adapted to at least partly surround the rotation body, such that the rotation body is retained by the retaining device in a manner allowing rotational movement of the rotation body in relation to the retaining device. The at least one position sensor is adapted for determining a position in at least two coordinates of the pattern of the rotation body. The at least one position sensor is located at, in or on the retaining device.

The term minimal invasive intervention as utilized herein comprises minimal invasive surgery, as described above. The term minimal invasive intervention as utilized herein also comprises other kinds of interventions. Examples of such interventions are endoscopy, i.e. looking inside the body, e.g. by means of the above-mentioned endoscope, biopsy or usage of a catheter.

The minimal invasive intervention may be performed on a body of a human being or an animal. Further in order to train surgeons or veterinarians before operating on a living being, interventions may be performed on a corpse of a dead human being or animal. It is also feasible to perform such interventions on training material, e.g. models made of rubber or plastic. Hence the arrangement as disclosed herein is not only suitable for real world minimal invasive interventions, but is also suitable for use in a surgical training apparatus. The arrangement may further be part of a medical simulator for performing training in virtual reality. In addition, the arrangement may be utilized when performing robotic surgery, i.e. using robotic systems to aid in surgical procedures. In that case, data determined by the position sensor may be used for providing feedback to the robotic control system.

The arrangement as disclosed herein has the advantage of being usable both for training purposes and in the real world when performing an intervention on a living being. The person utilizing the arrangement will therefore experience a smooth transfer between a training situation and a real patient situation. The same or a similar medical instrument may be used both during training and during real world minimal invasive intervention. Thereby it is possible to measure and follow a learning curve for the person performing training. The same medical instrument can be used in virtual reality, for training on model materials, for training on corpses, for interventions on patients and for robotic surgery. There may thus be an authentic situation during the whole training. Further, there will be no steps in the learning curve when changing between different training environments, as is the case with today's training methods, since with the arrangement as disclosed herein, the same medical instrument may be used in the different training environments. By utilizing the arrangement as disclosed herein for training of the surgeon, he or she will have obtained a certain level of skill before operating on patients. Today, it may occur that a surgeon actually trains on the first patients while improving his or her skill, but with an arrangement as disclosed herein that level may be reached before the surgeon starts operating on real patients.

The arrangement is configured such that the components comprised therein, which are to be in contact or adjacent to the body on which the minimal invasive intervention is performed, can be adequately cleaned or sterilized. The materials may be chosen to be adequate for cleaning or sterilization. Purely as an example, the arrangement may be dismantled by disconnecting the position sensor from the retaining device or the position sensor may form a proximal portion of the retaining device, which may be disconnected from a distal portion. Thereafter the rotation body, the retaining device, or its distal portion, and the medical instrument may be run in a cleaning process, such as a sterilization process, e.g. in an autoclave. As an alternative, the rotation body, the retaining device and/or the medical instrument may be for single use, e.g. being disposed of after usage. This contributes to the versatility of the arrangement, such that it is suitable both for training, as described above, and for real world minimal invasive intervention.

Examples of medical instruments are instruments for grasping, suturing, suction, irrigation, extraction, cutting, coagulation, stapling or viewing. The term medical instrument as used herein further comprises instruments used for other interventions, such as an endoscope, a biopsy needle, a veress needle or a catheter. A medical instrument adapted for minimal invasive intervention may be used together with a trocar, through which the medical instrument is inserted. The trocar typically comprises an obturator and a cannula. The term medical instrument, as used herein, may also comprise the combination of a medical instrument and a trocar. As mentioned above, the instrument may be introduced through a tiny incision in the skin. The instrument may also be introduced orally or anally.

When performing certain operations, such as neuro operations or endonasal operations, it is important to know the position of the medical instrument in order to minimize or avoid the risk of damage to the patient. By e.g. placing the arrangement in a known position relative to the skull of the patient, the arrangement as disclosed herein is able to accurately determine the position of the instrument.

The term shaft as used herein comprises both rigid shafts and flexible shafts. It is e.g. known to the skilled person that medical instruments used for endoscopy may have flexible shafts. Purely as an example a shaft of an endoscope used for gastroscopy, bronchoscopy or colonoscopy may be flexible. A catheter may comprise a stiff shaft or a flexible shaft, while a biopsy needle or a veress needle comprises a stiff shaft.

The pattern may cover a portion of the surface of the rotation body, a main portion of its surface or substantially the entire surface. The pattern is preferably located on an outer surface of the rotation body. However, if the rotation body is at least partly transparent, e.g. comprising openings or being of a transparent material, there may, as an alternative or a complement, be a pattern on an inside surface, e.g. on a wall of a hole in the rotation body, or in an interior of the rotation body.

The pattern provides information for determining a position of the pattern by the position sensor. The pattern may be deliberately added to the surface of the rotation body. The pattern may be printed or laser-engraved on the surface of the rotation body. The pattern on the rotation body may be an optical pattern or a magnetic pattern. The pattern is used to determine a position of the shaft of the medical instrument. By knowing the properties of the shaft, e.g. its length, it is thereby possible to determine a position of a tip of the shaft and hence follow the actions of the surgeon.

The pattern on the rotation body may comprise information about position in absolute coordinates. Preferably the pattern itself comprises information about where on the surface of the rotation body a certain element of the pattern is located. The pattern thus preferably comprises information how different pattern elements are located in relation to each other. Examples of such patterns are known from EP 1963786 B1 disclosing a pattern comprising a plurality of pattern groups, wherein a pattern group comprises at least one node point and at least one information point. The node points are used for determining the position in the camera window, while information points are used for determining the absolute position of the pattern group. This kind of pattern further differs from some prior art patterns, which are able to measure relative positions, e.g. as a relative displacement, but where the pattern elements lack information about in which part of the pattern they are located.

The position of the pattern on the rotation body is determined in relation to the retaining device in at least two coordinates. The two coordinates may relate to two different coordinate axes, which preferably are orthogonal, e.g. Cartesian coordinate axes x and y. The two coordinates may then represent a rotation in x-direction and in y-direction of the rotation body. As an alternative, the two coordinates may e.g. represent rotation in z-direction and translation in z-direction. It has been found when comparing a beginner to an expert that the largest differences may be found in two coordinates, e.g. x-rotation and y-rotation. Hence, it may be sufficient to follow two coordinates in order to follow up the training, although three coordinates may be useful for a more accurate follow-up.

The position of the pattern of the rotation body may be determined in at least three coordinates. The three coordinates relate to a three-dimensional space. They may relate to a Cartesian coordinate system, a spherical coordinate system or a cylindrical coordinate system. Utilizing three coordinates is useful when utilizing the arrangement for determining a 3-dimensional position of the medical instrument. It is also useful for follow-up of training or for quality assurance.

A portion of the shaft of the medical instrument may itself form the rotation body or a sleeve adapted to be located around the medical instrument may form the rotation body.

The rotation body may comprise a hole with an axial direction for receiving the shaft of the medical instrument. The hole allows an axial displacement of the shaft in the axial direction relative to the rotation body. If a trocar is utilized as the medical instrument, the rotation body is adapted for receiving the shaft of the trocar, which in turn is adapted for receiving the shaft of another medical instrument. The hole may go through the rotation body, i.e. be a through-going hole. The hole may pass a centre of the rotation body. The hole suitably is substantially straight having a diameter adapted to the outer diameter of the shaft of the medical instrument. The hole allows movement of the medical instrument in the axial direction of the hole, i.e. a linear translation in relation to the rotation body.

Alternatively, dependent on configuration of the arrangement, the retaining device may comprise a hole with an axial direction for receiving the shaft of the medical instrument. The hole may go through the retaining device, i.e. be a through-going hole. The hole allows an axial displacement of the shaft in the axial direction relative to the retaining device. In that case the retaining device may constitute a bearing for the medical instrument, which is further described below.

At least a portion of an outer surface of the rotation body may follow a spherical contour. Preferably a main portion of the surface, or substantially the entire surface, may follow the spherical contour. Purely as an example, the rotation body may have the contour of a sphere with a hole passing the centre of the sphere. The pattern may then be located on the outer surface of the sphere. The spherical contour has been found to be advantageous, since the rotation body then may be utilized as a ball joint, located outside but adjacent to the body of the patient and facilitating precise movement of the medical instrument inside the body of the patient. The spherical contour allows movements in all three dimensions of the medical instrument. If combined with the hole of the rotation body as described above, the medical instrument may be rotated around the rotation body as a ball joint and linearly translated along the axial direction through the hole. In addition, the medical instrument may be rotated around its longitudinal axis, i.e. around an axis of the shaft.

As an alternative to the spherical contour, at least a portion of an outer surface of the rotation body may follow a cylindrical contour. Preferably a main portion of the surface or substantially the entire surface may follow the cylindrical contour. Purely as an example, the rotation body may have the contour of a cylinder with a hole passing the centre of the cylinder. The pattern may then be located on the outer surface of the cylinder. The rotation body may also be in the form a sleeve adapted to be located around the medical instrument or the rotation body may form a portion of the shaft, e.g. in case the retaining device provides the hole. The cylindrical contour allows rotation around the longitudinal cylinder axis. If combined with the hole as described above, and assuming that the cylinder axis coincides with the axial direction of the hole, the medical instrument may be rotated around its cylinder axis and linearly translated along the cylinder axis.

The relative movability between the parts of the arrangement, e.g. between two or more of the rotation body, the shaft of the medical instrument and the trocar, i.e. if they are fixed to each other or rotatable in relation to each other, may be selected dependent on the desired number of coordinates used to determine the position of the pattern of the rotation body and of an axial position, as is further described below, i.e. the desired number of degrees of freedom. The shaft of the medical instrument may e.g. be torsional-rigidly connected to the rotation body in such a way that a rotation of the shaft is transferred to the rotation body. The shaft may be directly connected to the rotation body or it may be connected to a trocar, which may be located between the shaft and the rotation body, with the shaft being torsional-rigidly connected to the rotation body via the optional trocar. The trocar may be torsional-rigidly connected to the shaft of the medical instrument, but may alternatively be cylindrically rotatable in relation to the rotation body. The shaft of the medical instrument may be cylindrically rotatable in relation to the trocar or may be fixed in relation to the trocar.

The at least one position sensor and the pattern of the rotation body may be adapted for determining the position of the pattern in three coordinates. The three coordinates relate to coordinate axes spanning a three-dimensional space, e.g. a Cartesian coordinate system, a spherical coordinate system or a cylindrical coordinate system.

By utilizing absolute coordinates and by determining the three-dimensional position of a pivot point for the rotational movement of the rotation body in relation to retaining device, the position of the pivot point being determined in relation to the surrounding environment, e.g. in relation to an operating room and/or the patient, the position of the medical instrument may be determined in absolute coordinates in relation to the surrounding environment. It may be assumed that the at least one position sensor is located in a known position in the retaining device with a known distance to the rotation body. It is then sufficient to determine the position of the pivot point once, e.g. as a calibration before the minimal invasive intervention starts. There is hence no need to continuously make such three-dimensional calibration during the minimal invasive intervention, since the absolute position of the medical instrument is known by knowing the position of the pivot point in relation to the surrounding environment, which position may be determined once, plus knowing the position of the rotation body in relation to the retaining device, which may be determined continuously or intermittently. Since the position of the retaining device in relation to the surrounding environment is determined once before the minimal invasive intervention starts, there is no risk that the patient, the surgeon, or any assisting staff in the operating room, would obscure position signals sent out from the medical instrument, which could be the case with some prior art arrangements utilizing a transmitter in the medical instrument.

The at least one position sensor may be a non-contact sensor. If more than one sensor is utilized they may be of different types. They may be located in an angled relationship to each other, e.g. perpendicular to each other.

The pattern may be an optical pattern and the at least one position sensor may be an optical position sensor, such as a camera. The camera may be of a two-dimensional kind. It may have a distance in the range of 1-50 mm from the pattern, preferably in the range of 5-40 mm and more preferably in the range of 10-30 mm.

As an alternative or a complement, the pattern may be a magnetic pattern and the at least one position sensor may be a magnetic sensor.

An optical pattern may be preferable, since detection of a magnetic pattern may be influenced by metal of the medical instrument, or the magnetic pattern may itself influence a medical instrument comprising metal.

The arrangement may further comprise a sensor for determining an axial position of the shaft. The axial position may be determined in relation to the rotation body, e.g. to the above-mentioned hole, and/or in relation to the retaining device. The sensor may be located in the rotation body or in the retaining device.

The sensor for determining an axial position of the shaft may be a linear sensor. The axial position sensor may be at least partly located inside the rotation body, e.g. at the wall of the hole. This may be the case when the rotation body follows a spherical contour. As an alternative, the axial position sensor may be located in the trocar. Purely as an example, at least a portion of the shaft of the medical instrument may comprise a conductive surface, while there may be a contact, e.g. a metal sphere, located at a surface of the wall of the hole or in the trocar. The sphere may be biased, e.g. by a spring, towards the shaft of the medical instrument. The sensor in that case functions as a slide resistor.

As an alternative to utilizing the above-described linear sensor for determining the axial position of the shaft, there may be a shaft pattern on the shaft of the medical instrument, or on a sleeve located around the shaft, the position of the shaft pattern being determinable by an axial position sensor. The shaft pattern in that case preferably is of the kind described above regarding the pattern on the rotation body. The axial position sensor may be a position sensor of the same kind as the position sensor for determining the pattern on the rotation body, e.g. a camera located within the rotation body, e.g. facing the hole and thus the shaft of the medical instrument or a camera located in the trocar. Thereby it is possible to determine an axial position of the shaft, and hence to determine a linear translation of the shaft.

The shaft pattern may also be utilized to determine rotation of the shaft around its length axis, e.g. by means of the camera.

If the rotation body is at least partly transparent, a single sensor, e.g. a single camera located in, on or at the retaining device, may be utilized both for determining the position of the pattern on the rotation body and for determining the position of the shaft pattern on the shaft of the medical instrument. Purely as an example, the rotation body may comprise or be constituted by a transparent material or the rotation body may comprise openings making it possible to look through the rotation body onto the shaft of the medical instrument. The same pattern, e.g. located along a portion of the shaft of the medical instrument, may be used both for determining rotation of the medical instrument and as the shaft pattern for determining linear translations, the shaft pattern in that case constituting the pattern of the rotation body, such that a single pattern is sufficient. Utilizing the shaft pattern is for example suitable when the rotation body follows a spherical contour and/or follows a cylindrical contour.

If a part of the shaft forms the rotation body, or if a sleeve on the shaft forms the rotation body, the axial position may be determined in relation to the retaining device. The rotation body may in that case follow a cylindrical contour.

If utilizing an instrument, of which at least a portion of the shaft, or the sleeve, comprises a shaft pattern, the shaft pattern may, as an alternative or as a complement to a common force sensor such as a strain gauge, be used for measuring tensioning of the shaft, e.g. when applying a force and/or a torque to the shaft, e.g. a torsional tension. The force and/or the torque may e.g. be applied by the surgeon handling the medical instrument. When the material of the shaft is tensioned, the appearance of the shaft pattern will change slightly. Depending on the type of tension, the shaft pattern may be compressed or extended and/or the shaft pattern may change its angular orientation. These changes of the shaft pattern may be utilized to determine the tension applied to the shaft. If comparing to the shaft pattern of an untensioned shaft and knowing material properties, absolute values for the tensioning may be determined. Material properties of the shaft may be determined by making calibration tests of the shaft before the medical instrument is placed in the arrangement, or at least before the use of the instrument starts, e.g. as a step in a production process.

The retaining device may provide a bearing for receiving the shaft and allowing the shaft to rotate 3-dimensionally in the bearing, the bearing also allowing axial translation relative to the bearing. In that case, the shaft may comprise a shaft pattern, or a sleeve with a shaft pattern may be located around the shaft. An inner surface of the retaining device may form the bearing. At least one position sensor, e.g. a camera, may be arranged to have a free view to the shaft pattern, e.g. through a transparent window. The at least one position sensor may view the shaft pattern in the plane of the bearing or in a plane slightly above or below the bearing. The shaft is free to move axially, i.e. up and down along the shaft through the retaining device. In addition, the shaft is rotatable in all three dimensions in the bearing, such that the shaft may be angled in relation to a neutral position of the shaft. Further, the shaft may rotate around the axis of the shaft. The bearing may be ring-shaped, i.e. form a ring around the shaft. In addition, the shaft pattern may be utilized for determining a tension applied to the shaft.

In such an arrangement, i.e. the retaining device forming a bearing for the shaft, the rotation body may form part of the shaft or the sleeve may form the rotation body. The same pattern, i.e. the shaft pattern, and the same position sensor, e.g. the camera, may hence be used for determining the rotation in the bearing and the axial position of the shaft and further for the rotation of the shaft around its longitudinal axis. In addition, the shaft pattern may be utilized for determining a tension applied to the shaft, as described above. This embodiment of the arrangement may be positioned very close to the skin of the patient. As an option, this arrangement may be comprised in the trocar.

This kind of arrangement, i.e. the retaining device forming a bearing for the shaft, is also appropriate for other applications than a minimal invasive intervention, e.g. as a joystick or as an input device for a computer game or an input devices for a vehicle, vessel or aircraft. The arrangement may further be used to determine how much a linear sensor located along the shaft, is angled in relation to a neutral position of the shaft. The arrangement may e.g. be used to determine if, or how much, an axis of a rotatable shaft in a bearing deviates from the intended axial direction. In that case the arrangement may constitute components of the bearing arrangement. The camera, or cameras, may then be located in the bearing housing. The arrangement may suitably be utilized in a spherical bearing. The sleeve may form an inner ring of a bearing. This kind of arrangement is also suitable for determining movements of a static shaft, e.g. a bolt used as a fastening means. The arrangement may suitably be used for properly aligning a rotatable shaft.

Two or more arrangements with the retaining device forming a bearing for the shaft may be located along the shaft of the same medical instrument. In that case, the axial position of the shaft and the rotation of the shaft around its longitudinal axis may be determined and, in addition, the shaft pattern may be utilized for determining a tension, e.g. a torsional tension, applied to the shaft. By utilizing two interspaced arrangements, the tension, e.g. the torsional tension, may be determined with high accuracy.

In a second aspect of the present invention, there is provided a medical instrument for minimal invasive intervention. The medical instrument comprises a shaft, at least a portion of the shaft comprises a pattern for determining a position of the shaft and hence of the medical instrument. Preferably the pattern of the shaft comprises information about position in absolute coordinates. Suitable patterns are described above.

In a third aspect of the present invention, there is provided a kit comprising an arrangement for minimal invasive intervention as disclosed herein and a medical instrument for minimal invasive intervention. The medical instrument comprises a shaft. As mentioned above, the term medical instrument, as used herein, also comprises a trocar, through which another medical instrument is inserted.

In case the rotation body comprises a hole as described herein, the medical instrument may be adapted to be arranged with the shaft going through the hole of the rotation body of the arrangement.

The rotation body may form a sleeve adapted to be located along, and at least partly around, a portion of the shaft of the medical instrument. The sleeve may be translationally movable in relation to the shaft allowing linear translation of the shaft or the sleeve may be fixedly attached to the shaft. As an alternative, or a complement, the rotation body may constitute a portion of the shaft of the medical instrument.

As mentioned above, the rotation body may be a separate unit, e.g. following the contour of a sphere or a cylinder adapted to be located around the shaft of the medical instrument. In that case the pattern is located on the surface of the rotation body.

A portion of the shaft, or a portion of the sleeve if located along the shaft of the medical instrument, may comprise a shaft pattern for determining a position of the shaft, as is described herein. Preferably the shaft pattern comprises information about position in absolute coordinates.

In a fourth aspect of the present invention, there is provided a system for follow-up of a minimal invasive intervention. The system comprises an arrangement for minimal invasive intervention as disclosed herein, or a kit for minimal invasive intervention as disclosed herein, and a memory for storing data of determined positions determined by the at least one position sensor. The system comprises one or more arrangements for minimal invasive intervention. The memory may be located in a central processing unit but may also be a separate unit. The memory may, as a complement or an alternative, be located in an external location, wiredly or wirelessly connected to the position sensor of the arrangement.

In a fifth aspect of the present invention, there is provided a method for determining a position of a medical instrument by means of an arrangement for minimal invasive intervention as disclosed herein, or a kit for minimal invasive intervention as disclosed herein. The method comprises
determining in at least two coordinates a position of the pattern on the surface of the rotation body by means of the at least one position sensor,
utilizing the determined position of the pattern to determine the position of the medical instrument.

As described above, the position of the pattern may be determined in three coordinates, preferably in absolute coordinates.

The method may further comprise
calibrating the position of a pivot point for the rotational movement of the rotation body in relation to the retaining device, the position of the pivot point being determined in relation to a surrounding environment, such as an operating room and/or a patient.

By determining the three-dimensional position of the pivot point for the rotational movement of the rotation body in relation to retaining device, the position of the pivot point being determined in relation to the surrounding environment, e.g. in relation to an operating room and/or the patient, the position of the medical instrument may be determined in absolute coordinates in relation to the surrounding environment. It is sufficient to determine the position of the pivot point once, e.g. as a calibration before a minimal invasive intervention starts. It is assumed that the at least one position sensor is located in a known position in the retaining device with a known distance to the rotation body. There is hence no need to continuously make such three-dimensional calibration during the minimal invasive intervention, since the absolute position of the medical instrument is known by knowing the position of the pivot point in relation to the surrounding environment, which position may be determined once, plus knowing the position of the rotation body in relation to the retaining device, which may be determined continuously or intermittently. Since the position of the retaining device in relation to the surrounding environment is determined once before the minimal invasive intervention starts, there is no risk that the patient, the surgeon, or any assisting staff in the operating room, would obscure position signals sent out from the medical instrument, which could be the case with some prior art arrangements utilizing a transmitter in the medical instrument.

The method may further comprise
determining an axial position of the shaft of the medical instrument in the hole,
utilizing the determined position of the pattern and the determined axial position to determine the position of the medical instrument.

Thereby both movements of the medical instrument around the rotation body, i.e. rotations, and linear translations may be determined. These steps may e.g. be performed if the medical instrument comprises a shaft and the rotation body comprises a hole with an axial direction for receiving the shaft.

In case a portion of the shaft, or the sleeve, comprises a shaft pattern for determining a position of the shaft, preferably the shaft pattern comprising information about position in absolute coordinates, the method may further comprise
utilizing the shaft pattern on the shaft or sleeve for determining a tension applied to the shaft or sleeve and/or for determining axial position of the shaft or the sleeve.

The method may further comprise
determining at least two positions of the medical instrument,
utilizing the at least two positions to determine a displacement of the medical instrument.

By knowing at least two positions, the displacement of the instrument between these two positions may be determined.

The method may further comprise
continuously or intermittently determining positions of the medical instrument,
utilizing the positions to determine the displacement motion of the medical instrument.

By continuously or intermittently determining positions of the medical instrument in the way disclosed herein the displacement motion, e.g. the displacement path, the displacement velocity, the displacement acceleration and/or the displacement smoothness, may be determined. The displacement velocity, the displacement acceleration and/or the displacement smoothness may be determined from the mathematical derivatives of the determined displacements. Further, in case the shaft or sleeve comprises a shaft pattern, the shaft pattern may be used for monitoring the tension applied to the shaft or sleeve.

The method may further comprise
storing data about the determined positions of the medical instrument, and
as an option, using the data for statistical follow-up.

The stored data may be used for follow-up of training of surgeons. In addition, or as a complement, stored data may be used for quality assurance and/or quality follow-up of minimal invasive intervention, e.g. of training interventions or real-world interventions.

BRIEF DESCRIPTION OF THE DRAWINGS

The present invention will hereinafter be further explained by means of non-limiting examples with reference to the appended drawings wherein.

It should be noted that the appended drawings are not necessarily drawn to scale and that the dimensions of some features of the present invention may have been exaggerated for the sake of clarity.

DETAILED DESCRIPTION

The invention will, in the following, be exemplified by embodiments. It should however be realized that the embodiments are included in order to explain principles of the invention and not to limit the scope of the invention, defined by the appended claims. Details from two or more of the embodiments may be combined with each other.

Figure 1:
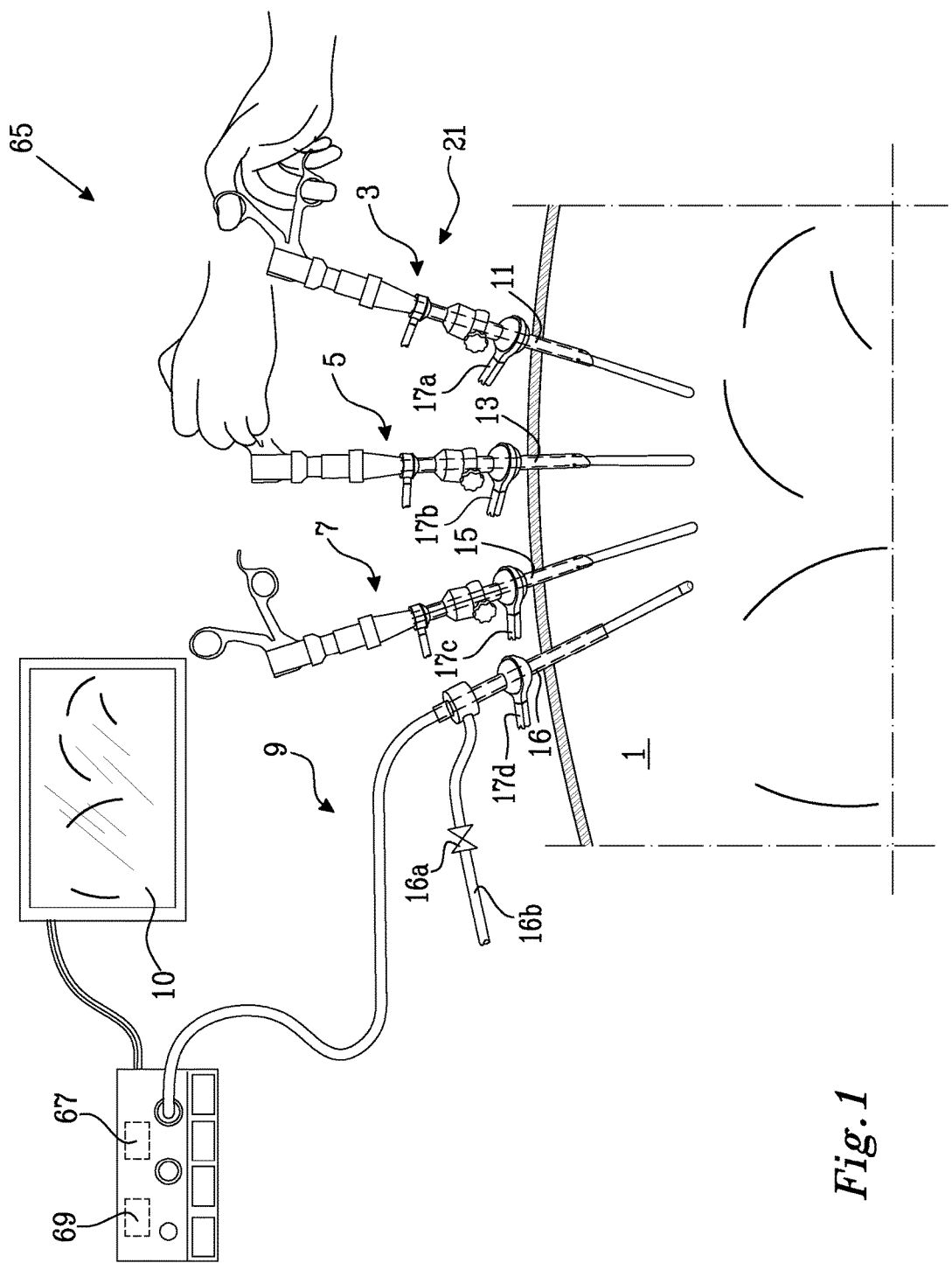
FIG. 1 is a schematic view of an ongoing minimal invasive intervention.

FIG. 1 illustrates an ongoing minimal invasive intervention in the form of a minimal invasive surgery in an abdomen of a patient 1, a so-called laparoscopic surgery. A surgeon performs the surgery through tiny incisions in the skin, often only a few millimeters, through which surgical instruments 3, 5, 7 are inserted. An endoscope 9 comprising a miniature camera attached to a light tube, i.e. another type of medical instrument, is inserted through one of the incisions to provide the surgeon a view of the minimal invasive intervention, which view is projected on a screen 10. The surgeon utilizes the instruments 3, 5, 7 and the endoscope 9 to e.g. explore what is wrong, remove unwanted objects or body parts and/or repair what is inside the body. The surgical instruments 3, 5, 7 are inserted through the skin into the body of the patient 1 through a hollow tube of a respective trocar 11, 13, 15, 16. However, as an alternative or a complement, one or more of the trocars 11, 13, 15, 16 may be dispensed with such that the medical instrument is directly inserted through the skin. The surgeon utilizes two of the surgical instruments 3, 5. The instruments 3, 5, 7, 9 are held by arrangements 17*a*, 17*b*, 17*c*, 17*d*, e.g connected to a stand, which arrangements are further described below. The trocar 16 of the endoscope 9 is provided with a gas supply, e.g. nitrogen. A valve 16*a* controls gas flow through a hose 16*b* connected to the trocar 16. Such gas supply may be connected to any of the trocars, but it is common to connect the gas supply to the trocar 16 of the endoscope 9. One or more of the other trocars 11, 13, 15 may be provided with non-return valves or seals in order to prevent the gas from going out through that trocar 11, 13, 15.

Figure 2:
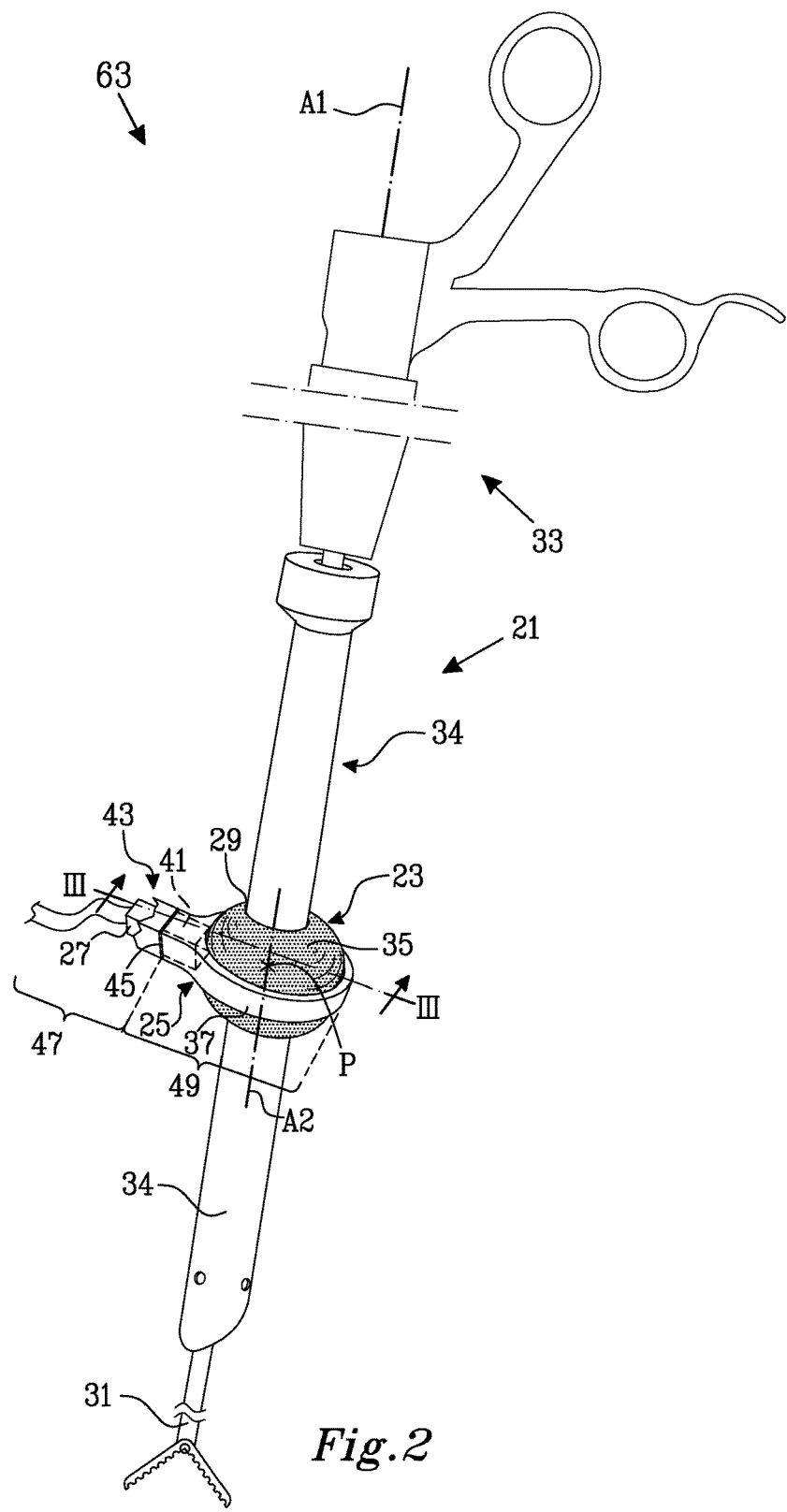
FIG. 2 is a view of an arrangement for minimal invasive intervention according to a first embodiment of the invention
Figure 3A:
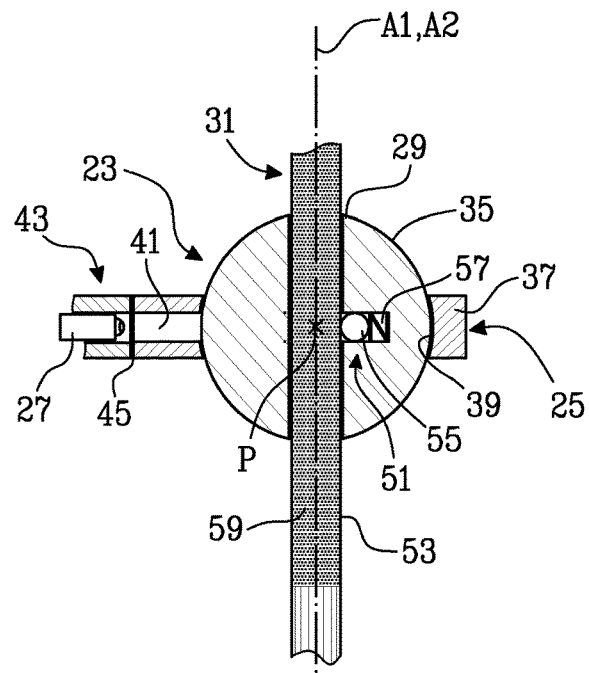
FIG. 3a-c are cross-sectional views of the arrangement of FIG. 2.
Figure 3B:
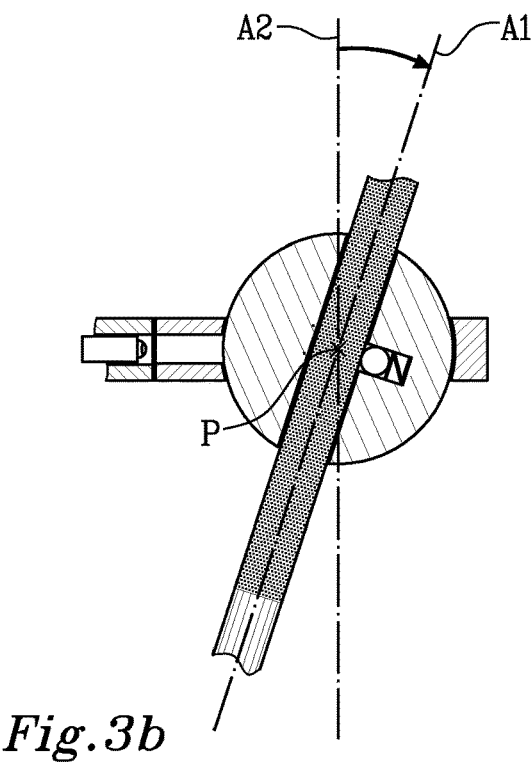
Figure 3C:
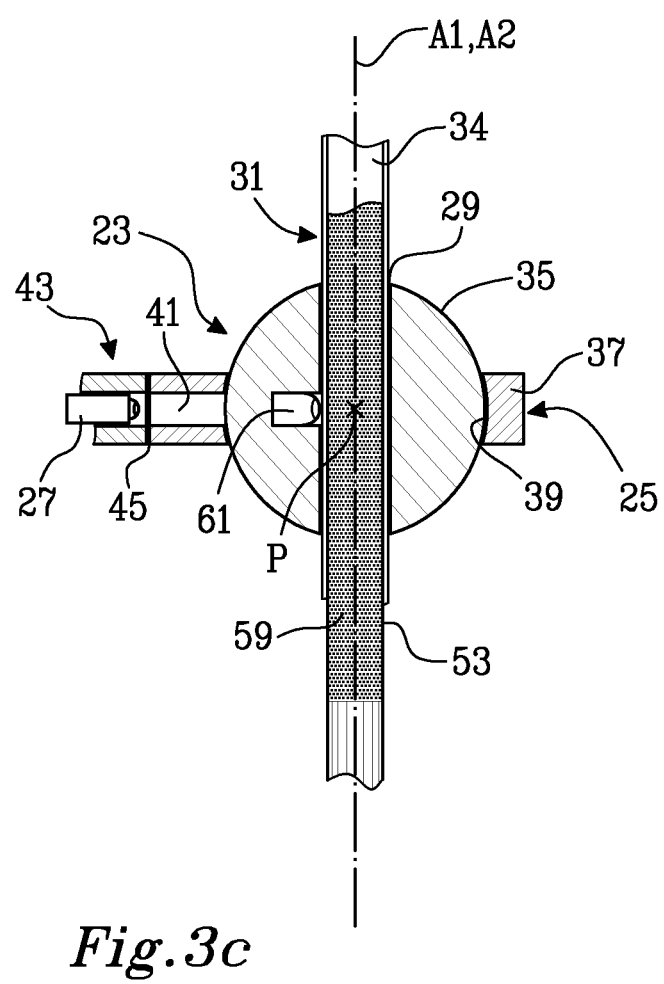

FIG. 2 is a detailed view of an arrangement 21 for minimal invasive intervention according to a first embodiment of the invention and FIGS. 3*a-c* are cross-sectional views of variants of the arrangement 21 of FIG. 2. One or more of the surgical instruments 3, 5, 7 and the endoscope 9 may be used together with an arrangement 21 according to the invention.

The arrangement 21 comprises a rotation body 23, a retaining device 25 and a position sensor 27. A main portion of the outer surface of the rotation body 23 follows a spherical contour. The rotation body 23 comprises a through-going hole 29 with an axial direction A1 for receiving a shaft 31 of a medical instrument 33, e.g. of one of the surgical instruments 3, 5, 7 or the endoscope 9. The through-going hole 29 allows an axial displacement of the shaft 31 in the axial direction A1 relative to the rotation body 23. In the illustrated embodiment the whole surface of rotation body 23, except for where the through-going hole 29 is located, follows a spherical contour.

FIG. 2 further illustrates a trocar 34, through which the shaft 31 of the medical instrument 33 is inserted. As an alternative, the trocar 34 may be dispensed with such that the medical instrument 33 is directly inserted into the rotation body 23.

On the outer surface of the rotation body 23 there is pattern 35. Preferably the pattern 35 itself comprises information about where on the outer surface of the rotation body 23 a certain element of the pattern 35 is located. Examples of such patterns are known from EP 1963786 B1. The pattern 35 may be an optical pattern or a magnetic pattern. An optical pattern is often preferable, since detection of a magnetic pattern may be influenced by metal of the medical instrument 33, or the magnetic pattern may itself influence the medical instrument 33.

By utilizing such a pattern 35 it is possible to determine the position of the rotation body 23 in relation to the retaining device 25 in absolute coordinates. Further, by determining the three-dimensional position of a pivot point P for the rotational movement of the rotation body 23 in relation to retaining device 25, the position of the pivot point P being determined in relation to the surrounding environment, e.g. in relation to an operating room and/or to the patient 1, the position of the medical instrument 33 may be determined in absolute coordinates in relation to the surrounding environment. It is sufficient to determine the position of the pivot point P once, e.g. as a calibration before a minimal invasive intervention starts. There is hence no need to continuously make such three-dimensional calibration during the minimal invasive intervention, since the absolute position of the medical instrument 33 is known by knowing the position of the pivot point P in relation to the surrounding environment, which position may be determined once, plus knowing the position of the rotation body 23 in relation to the retaining device 25, which may be determined continuously or intermittently. Since the position of the retaining device 25 in relation to the surrounding environment is determined once before the minimal invasive intervention starts, there is no risk that the patient 1, the surgeon, or any assisting staff in the operating room, would obscure position signals sent out from the medical instrument, which could be the case with some prior art arrangements utilizing a transmitter in the medical instrument.

The above-suggested kind of pattern further differs from some prior art patterns, which are able to measure relative positions, e.g. as a relative displacement, but where the pattern elements lack information about in which part of the pattern they are located.

The retaining device 25 is adapted to at least partly surround the rotation body 23, such that the rotation body 23 is retained by the retaining device 25 in a manner allowing rotational movement of the rotation body 23 in relation to the retaining device 25. See FIGS. 3*a* and 3*b*, where the rotation body 23 has rotated about 20 degrees between the two views. The above-mentioned pivot point P for the rotation is located in the three-dimensional space defined by the retaining device 25, but in the free air inside of the retaining device 25. The retaining device 25 has an axial direction A2 going through the pivot point P. In a neutral position of the rotation body 23, as in FIG. 3*a*, the axes A1 of the rotation body 23 and A2 of the retaining device 25 coincide. However, in FIG. 3*b* the two axes A1 and A2 differ by the about 20 degrees.

The retaining device 25 may comprise a housing, not illustrated, partially encircling the rotation body 23. The housing would in that case comprise an opening angle α allowing movement of the rotation body 23. The opening angle α may be centred around the axial direction A2 of the retaining device 25. The opening angle α may be chosen to be at least 25 degrees, preferably at least 30 degrees, more preferably at least 35 degrees and most preferably at least 40 degrees. The opening angle α is hence chosen to make it possible to move the instrument inside the body of the patient 1 in a desired way.

As an alternative to a housing, the retaining device 25 may comprise a ring-shaped component 37 encircling the rotation body 23, as in the illustrated embodiment. The cross-section of the ring-shaped component 37 has a non-straight inner surface 39 adapted to retain the rotation body 23 in the retaining device 25. The inner surface 39 may have a cross-sectional curvature corresponding to that of the outer surface of the rotation body 23 but with a slightly larger radius. See the cross-sectional view of FIG. 3a. As an alternative, the cross-section of the inner surface 39 may comprise a plurality of straight lines, e.g. two. The cross-section of the inner surface 39 is adapted to retain the rotation body 23 in the retaining device 25. The ring-shaped component 37 allows a greater opening angle α as compared to the above-described housing.

The arrangement 21 further comprises the at least one position sensor 27 for determining a position in at least two coordinates of the pattern 35 on the outer surface of the rotation body 23. The at least one position sensor 27 is located at, in or on the retaining device 25, such that it has a free view onto the pattern 35. The at least one position sensor 27 is wiredly or wirelessly connected to a system 65, which system 65 is further described below. In the illustrated example, the at least one position sensor 27 comprises a camera, which is located in the retaining device 25. The camera has a free field of view through a channel 41 in a handle portion 43 of the retaining device 25. The camera is used to determine the position of the pattern 35 on the surface of the rotation body 23. The camera may be of a two-dimensional kind. It may have a distance in the range of 1-50 mm from the pattern, preferably in the range of 5-40 mm and more preferably in the range of 10-30 mm. It is preferred to use a non-contact sensor, such as the illustrated camera.

The retaining device 25 can be disconnected at a connection 45 into a proximal portion 47 and a distal portion 49. The proximal portion 47 then comprises the at least one position sensor 27, i.e. the camera, and the electrical wiring of the camera. The distal portion 49 comprises the ring-shaped component 37. The distal portion 49, which is adapted to be closest to the patient 1, may be efficiently cleaned or sterilized, while the proximal portion 47 may be cleaned in a more lenient way. The rotation body 23, the distal portion 49 of the retaining device 25, and the medical instrument 33 may e.g. be run in a cleaning process, such as a sterilization process, e.g. in an autoclave.

As an option, there may be a linear sensor 51 located inside the rotation body 23, as may be gleaned from FIG. 3a, illustrating an example of a linear sensor 51. In that case, at least a portion 53 of the shaft 31 of the medical instrument 33 adapted to go through the through-going hole 29 comprises a conductive surface, while there is a contact, e.g. a metal sphere 55 located at a surface of the through-going hole 29. The sphere 55 is biased, e.g. by a spring 57, towards the through-going hole 29 and hence towards the shaft 31 of the medical instrument 33. In this example, the trocar is dispensed with. The linear sensor 51 in that case functions as a kind of slide resistor. The linear sensor 51 is connected to the system 65, e.g. in a way as described below in conjunction with FIG. 5.

As an alternative to, or a complement to, utilizing the linear sensor 51 illustrated in FIG. 3a, there may be a shaft pattern 59 on the shaft 31 of the medical instrument 33 or on a sleeve mounted on the shaft 31, the position of the shaft pattern 59 being determinable by an axial position sensor 61. See FIG. 3c illustrating an example with a transparent trocar 34, e.g. made of plastics. The shaft pattern 59 preferably is of the kind of pattern described above regarding the pattern 35 on the rotation body 23. The axial position sensor 61 may be a camera located within the rotation body 23, e.g. facing the through-going hole 29 and thus the shaft 31 of the medical instrument 33. Thereby it is possible to determine an axial position of the shaft 31 and hence to determine a linear translation of the shaft 31 in relation to the rotation body 23. If the rotation body 23 is at least partly transparent, a single sensor, e.g. a single camera, may be utilized both as the position sensor for determining the position of the pattern 35 on the rotation body 23 and as the axial position sensor for determining the position of the shaft pattern 59 on the shaft 31 of the medical instrument 33. Purely as an example, the rotation body 23 may comprise or be constituted by a transparent material or the rotation body 23 may comprise openings making it possible to look through the rotation body 23 onto the shaft 31 of the medical instrument 33.

If utilizing an instrument 33 where at least a portion of the shaft 31 comprises the shaft pattern 59, the shaft pattern 59 may be used for measuring tensioning of the shaft 31, e.g. when applying a force and/or a torque to the shaft 31. The force and/or the torque may be applied by the surgeon handling the medical instrument 33. When the material of the shaft 31 is tensioned, the appearance of the shaft pattern 59 will change slightly. Depending on the type of tension, the shaft pattern 59 may be compressed or extended and/or the shaft pattern 59 may change its angular orientation. These changes of the shaft pattern 59 may be determined to determine the tension applied to the shaft 31. If comparing to the shaft pattern 59 of an untensioned shaft 31 and knowing material properties, absolute values for the tensioning may be determined. Material properties of the shaft 31 may be determined by making calibration tests of the shaft 31 before the medical instrument 33 is placed in the arrangement 21, e.g. as a step in a production process.

The medical instrument 33 and the arrangement 21 form part of a kit 63. See FIG. 2. The medical instrument 33 may be an instrument for grasping, suturing, suction, irrigation, extraction, cutting, coagulation, stapling or viewing. The term medical instrument as used herein further comprises instruments used for other interventions, such as an endoscope, a biopsy needle, a veress needle or a catheter.

Going back again to FIG. 1 it can be seen that the arrangement 21 is part of the system 65, which is a system for follow-up of the minimal invasive intervention. The system 65 comprises one or more arrangements 21 as disclosed herein, or one or more kits 63 as disclosed herein, and a memory 67 for storing data of determined positions. The memory may be located in a central processing unit 69 but may also be a separate unit. The memory 67 may, as a complement or an alternative, be located in an external location.

Figure 4:
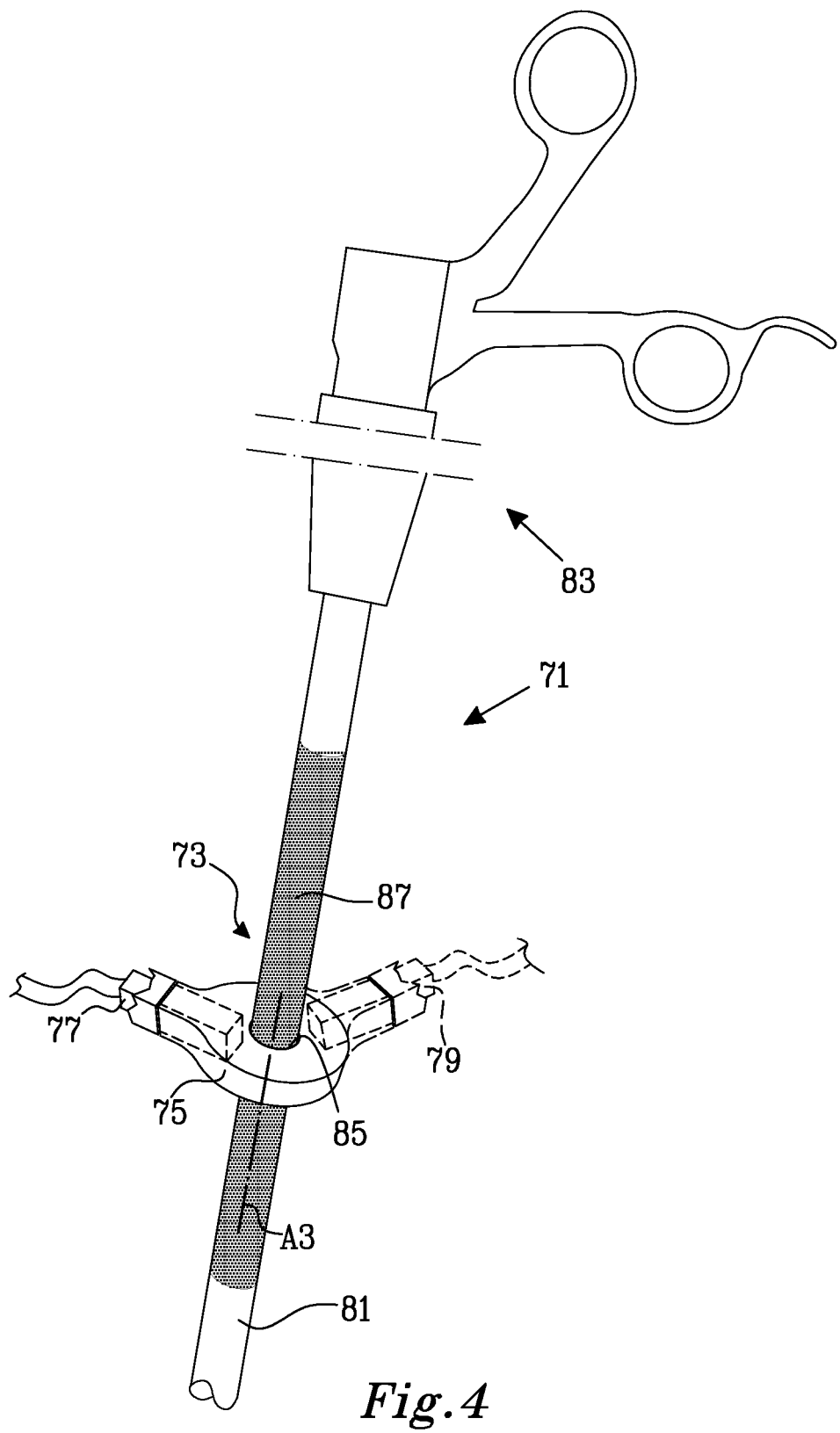
FIG. 4 is a view of an arrangement according to a second embodiment.

FIG. 4 illustrates an arrangement 71 for minimal invasive intervention according to a second embodiment of the invention. The arrangement 71 comprises a rotation body 73, a retaining device 75 and a position sensor 77. The rotation body 73 may be in the form of a cylindrical sleeve adapted to receive a medical instrument, or the rotation body 73 may form part of a shaft 81 of the medical instrument 83, as is illustrated in FIG. 4.

As an option, there may be a second position sensor 79, located at an angle to the position sensor 77, e.g. at a right angle in relation to the position sensor 77, as is indicated by dashed lines in FIG. 4.

The outer surface of the rotation body 73 follows a cylindrical contour. The retaining device 75 comprises a through-going hole 85 with an axial direction A3 for receiving the shaft 81. The through-going hole 85 allows an axial displacement of the shaft 81 in the axial direction A3 relative to the retaining device 75.

On at least a portion of the outer surface of the rotation body 73, i.e. for this embodiment on the shaft 81, there is a pattern 87. Examples of such patterns are known from EP 1963786 B1 and are described above in conjunction with FIG. 2. By utilizing such a pattern 87, it is possible to determine the position of the rotation body 73 in relation to the retaining device 75 in absolute coordinates.

The cylindrical contour allows rotation of the medical instrument 83 around the axis A3 in relation to the retaining device 75 and linear translations along the axis A3.

Figure 5:
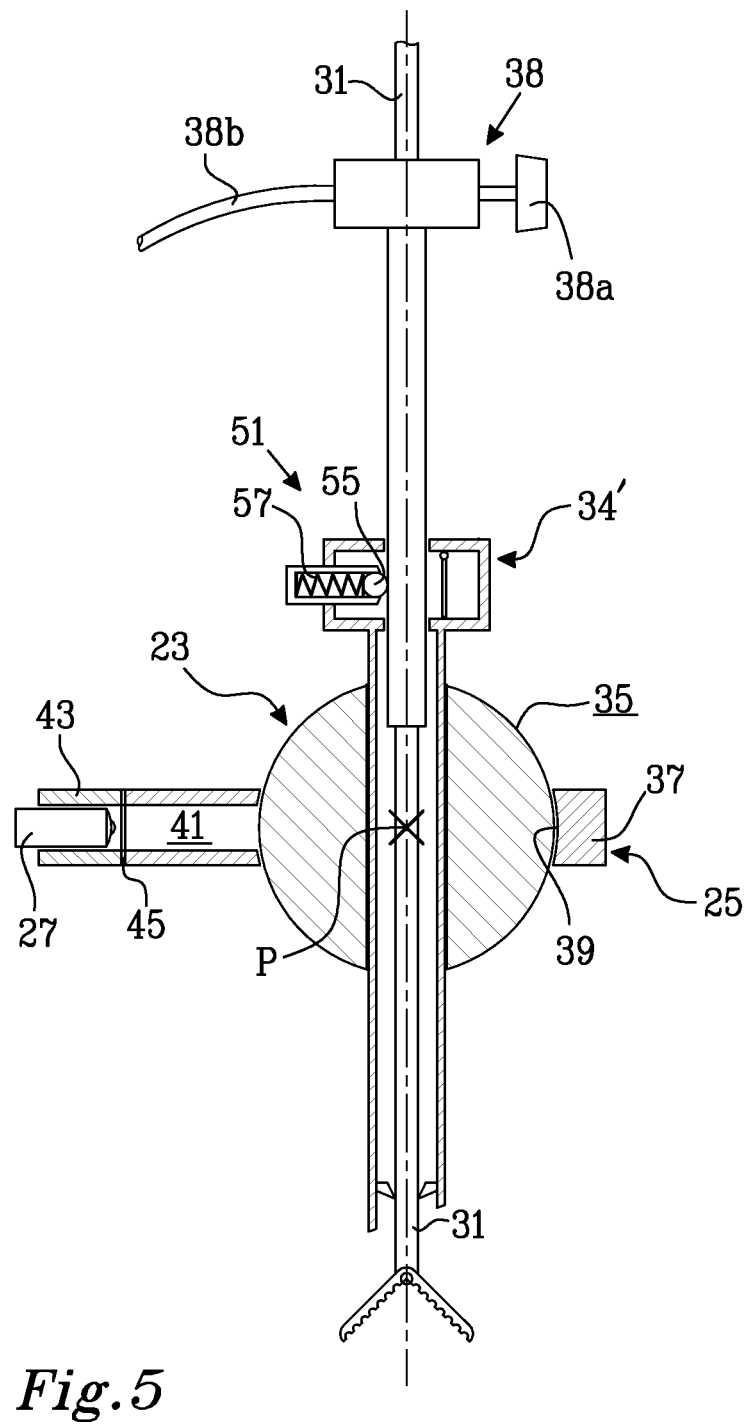
FIG. 5 is a view of an arrangement according to a third embodiment.

FIG. 5 illustrates an arrangement for minimal invasive intervention according to a third embodiment of the invention. Many details of the rotation body 23 and the retaining device correspond to that of the first embodiment and will not be described again. However, there are some differences, as described below.

In the third embodiment, the axial position sensor 51 is comprised in the trocar 34' and is located above the rotation body 23. The shaft 31 of the medical instrument is inserted into a sleeve 38. The linear sensor 51 operates in the way described above in conjunction with FIG. 3a. The sphere 55 abuts against the sleeve 38, which has a conductive surface. The sleeve 38 is locked to the shaft 31 of the medical instrument by a locking means 38a. The sleeve 38 and the sphere 55 together form a slide resistor, which is used for determining the axial position of the shaft 31. The slide resistor is connected by an electrical wire 38b to the system 65.

Figure 6:
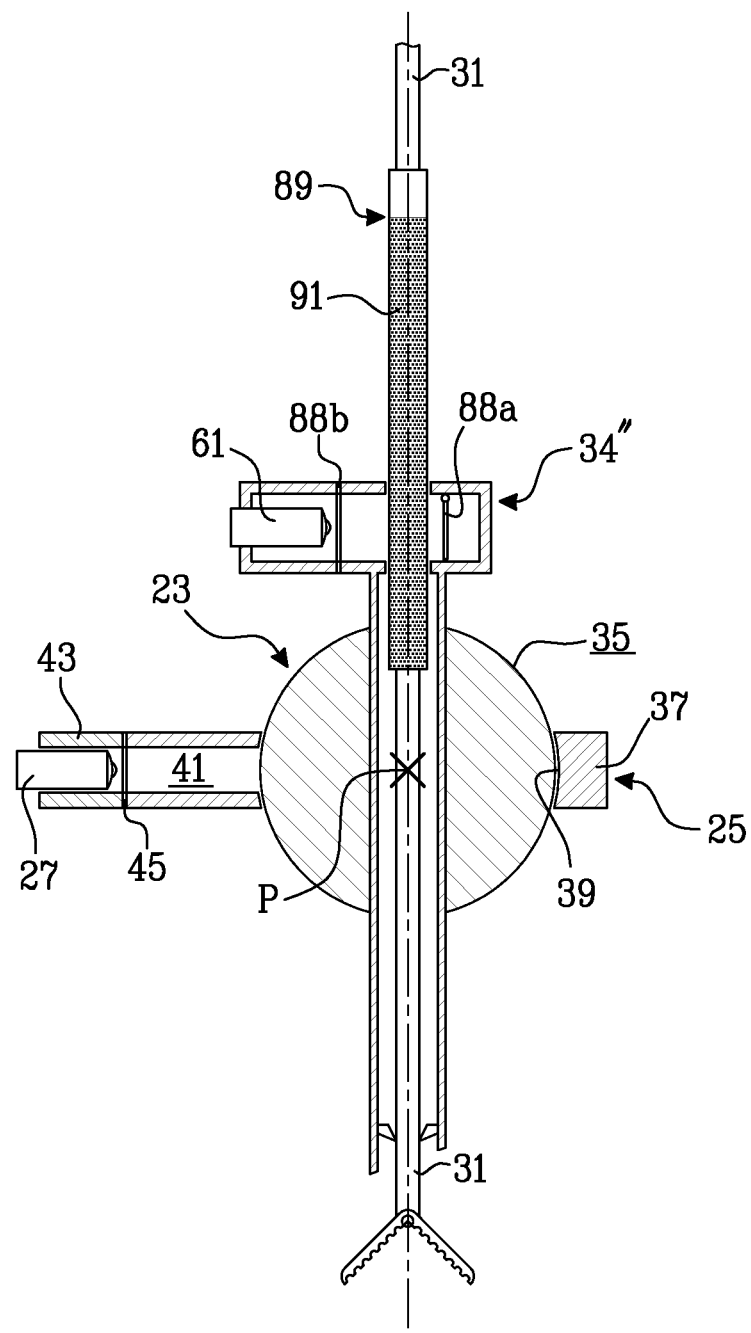
FIG. 6 is a view of an arrangement according to a fourth embodiment.

FIG. 6 illustrates an arrangement for minimal invasive intervention according to a fourth embodiment of the invention. Similar as for the third embodiment, the axial position sensor is comprised in the trocar 34", but in this embodiment, the axial position sensor comprises a camera 61, as described above in conjunction with FIG. 3c. The trocar also optionally comprises seals 88a, 88b, which e.g. may stop gas from leaving the trocar 34". There is a sleeve 89 comprising a shaft pattern 91 located around the shaft 31 of the medical instrument and the camera 61 utilizes the shaft pattern 91 to determine the axial position of the shaft. The sleeve 89 is locked to the shaft 31, such that it follows the shaft 31 when moving axially. As an alternative the shaft pattern could be located directly on the surface of the shaft 31 and the sleeve 89 may then be dispensed with.

Figure 7A:
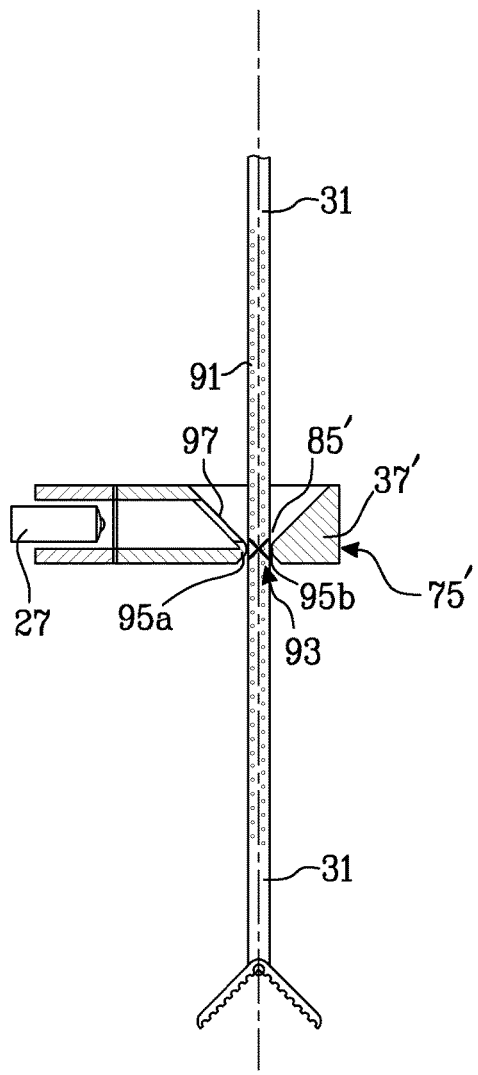
FIG. 7*a-b* are views of an arrangement according to a fifth embodiment.

FIG. 7 illustrates an arrangement for minimal invasive intervention according to a fifth embodiment of the invention. There is a shaft pattern 91 located directly on the surface of the shaft 31. As an alternative a sleeve 89 similar to that of the fourth embodiment may be utilized. The camera 27 utilizes the shaft pattern 91 to determine the axial position of the shaft 31.

Figure 7B:
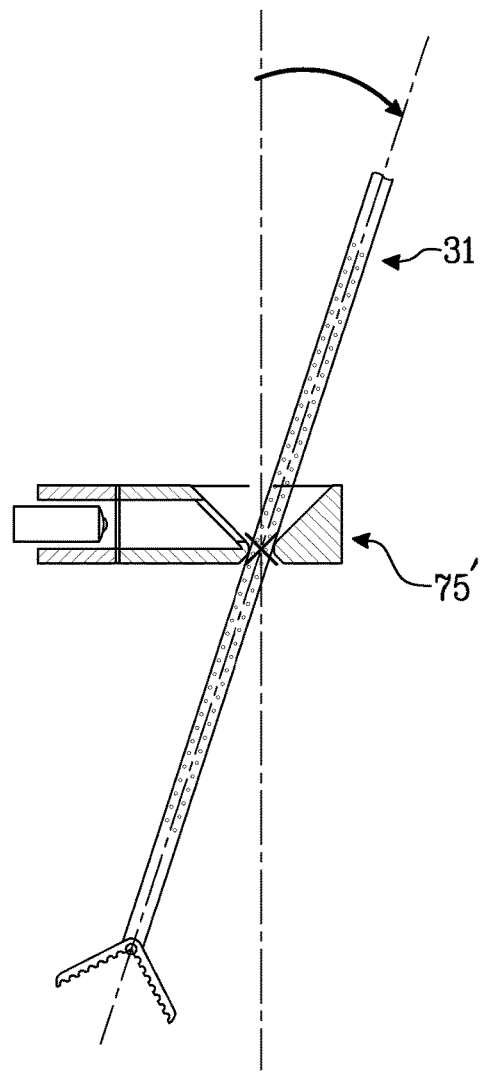

The fifth embodiment differs from the first to fourth embodiments in that the retaining device 75' allows the shaft 31 to rotate 3-dimensionally in a bearing 93 formed by an inner surface of the retaining device 75' and which bearing 93 in this exemplary embodiment is ring-shaped. See FIGS. 7a and 7b. In the cross-sectional view of FIG. 7a, the ring-shaped bearing 93 is seen as two tip-shaped abutments 95a, 95b of the ring-shaped component 37'. At least one position sensor 27, e.g. a camera, has a free view to the shaft pattern 91, e.g. through a transparent window 97. The at least one position sensor may view the shaft pattern 91 in the plane of the ring-shaped bearing 93 or in a plane slightly above, as is illustrated, or below. The shaft 31 is free to move axially, e.g. up and through the retaining device 75'. In addition, the shaft 31 is rotatable in all three dimensions around the ring-shaped bearing 93. See FIG. 7b illustrating the shaft 31 in an angled position as compared to the neutral axial position of FIG. 7a. In addition, the shaft 31 may rotate around its longitudinal axis. The rotation body forms part of the shaft 31. The same pattern, i.e. the shaft pattern 91, and the same position sensor 27, the camera, may hence be used for determining the rotation in the ring-shaped bearing 93, as in FIG. 7b, the axial position of the shaft and the rotation of the shaft 31 around its longitudinal axis. In addition, the shaft pattern 91 may be utilized for determining a tension applied to the shaft 31, as described above.

The arrangement of the fifth embodiment is also appropriate for other applications than a minimal invasive intervention, e.g. as a joystick or as an input device for a computer game or an input devices for a vehicle, vessel or aircraft. The arrangement may further be used to determine how much a linear sensor, located along the shaft, or the shaft, is angled.

Figure 8:
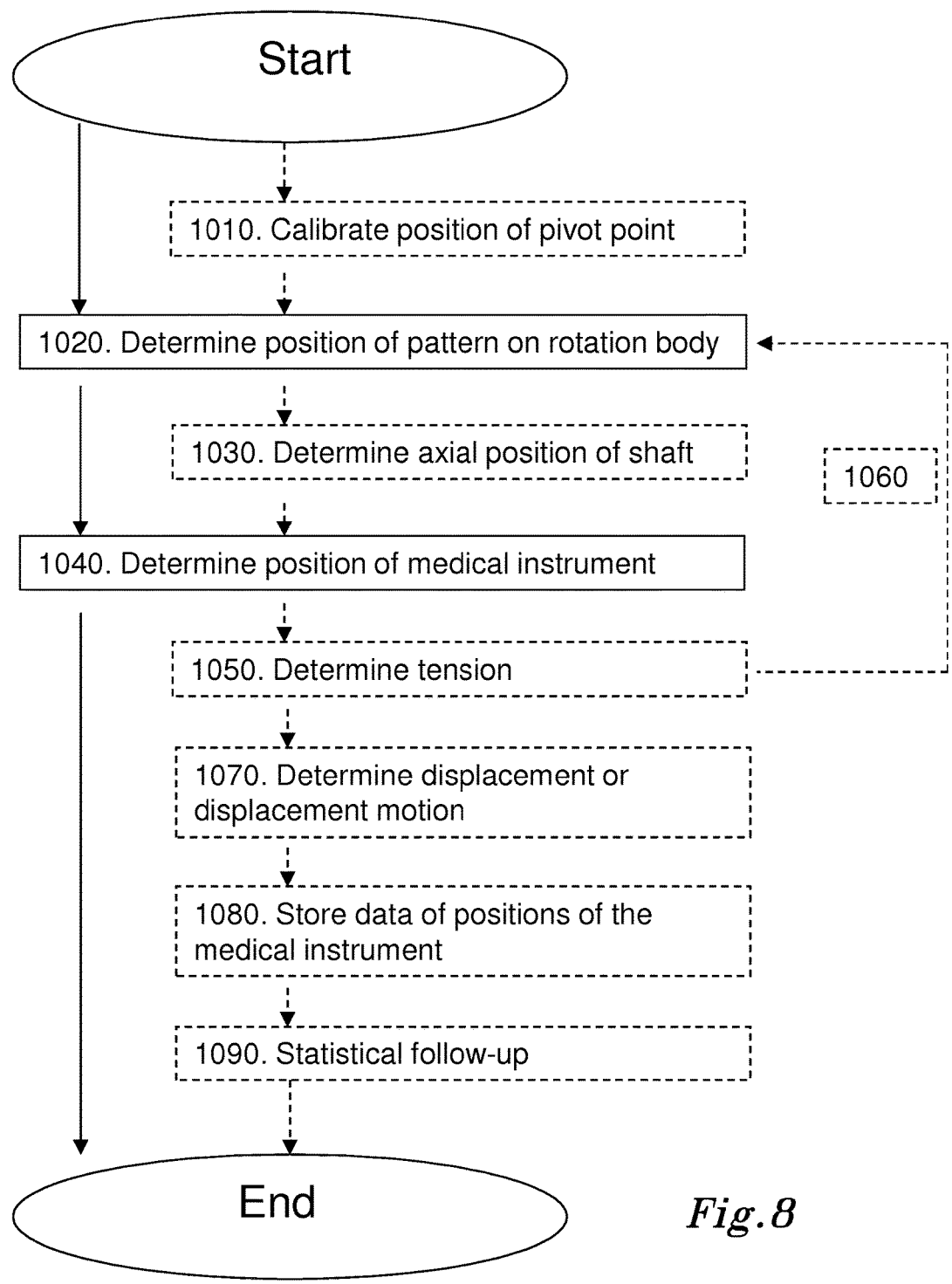
FIG. 8 illustrates a flowchart of a method according to the invention.

FIG. 8 illustrates a method according to the invention for determining a position of a medical instrument by means of an arrangement for minimal invasive intervention as disclosed herein, or a kit for minimal invasive intervention as disclosed herein. Method steps with dashed contour lines are optional, as is further described below.

In a minimal version, see boxes with unbroken contour lines in FIG. 5, the method comprises 1020. Determining in at least two coordinates a position of the pattern on the surface of the rotation body by means of the at least one position sensor.

1040. Utilizing the determined position of the pattern to determine the position of the medical instrument.

As described above, the position of the pattern may be determined in three coordinates, preferably in absolute coordinates.

The method may further comprise

1010. Calibrating the position of a pivot point for the rotational movement of the rotation body in relation to the retaining device, the position of the pivot point being determined in relation to a surrounding environment, such as an operating room and/or a patient.

By determining the three-dimensional position of the pivot point for the rotational movement of the rotation body in relation to retaining device, the position of the pivot point being determined in relation to the surrounding environment, e.g. in relation to an operating room and/or the patient, the position of the medical instrument may be determined in absolute coordinates in relation to the surrounding environment. It is sufficient to determine the position of the pivot point once, e.g. as a calibration before a minimal invasive intervention starts. It is assumed that the at least one position sensor is located in a known position in the retaining device with a known distance to the rotation body. There is hence no need to continuously make such three-dimensional calibration during the minimal invasive intervention, since the absolute position of the medical instrument is known by knowing the position of the pivot point in relation to the surrounding environment, which position may be determined once, plus knowing the position of the rotation body in relation to the retaining device, which may be determined continuously or intermittently. Since the position of the retaining device in relation to the surrounding environment is determined once before the minimal invasive intervention starts, there is no risk that the patient, the surgeon, or any assisting staff in the operating room, would obscure position signals sent out from the medical instrument, which could be the case with some prior art arrangements utilizing a transmitter in the medical instrument.

The method may further comprise

1030. Determining an axial position of the shaft of the medical instrument in the hole. In that case step 1040 comprises utilizing both the position of the pattern on the rotation body and the axial position:

1040. Utilizing the determined position of the pattern and the determined axial position to determine the position of the medical instrument.

Thereby movements of the medical instrument around the rotation body, i.e. rotations, and linear translations may be determined. These steps 1030, 1040 may e.g. be performed if the medical instrument comprises a shaft and the rotation body comprises a hole with an axial direction for receiving the shaft.

In case a portion of the shaft, or the sleeve, comprises a shaft pattern for determining a position of the shaft, preferably the shaft pattern comprising information about position in absolute coordinates, the method may further comprise 1050. Utilizing the shaft pattern on the shaft or sleeve for determining a tension applied to the shaft or sleeve and/or for determining axial position of the shaft or the sleeve.

Step 1050 may be performed before, in parallel to or after step 1040.

The method may further comprise
determining at least two positions of the medical instrument,
utilizing the at least two positions to determine a displacement of the medical instrument.

By knowing at least two positions, the displacement of the instrument between these two positions may be determined. This is illustrated in FIG. 5 by arrow 1060 going back to step 1020. As mentioned above, it is sufficient to perform step 1010 once, although step 1010 optionally may be repeated as well.

The method may further comprise
continuously or intermittently determining positions of the medical instrument. This is illustrated in FIG. 5 by the arrow 1060 going back to step 1020.

The method then further comprises:

1070. Utilizing the positions to determine the displacement motion of the medical instrument.

By continuously or intermittently determining positions of the medical instrument in the way disclosed herein the displacement motion, e.g. the displacement path, the displacement velocity, the displacement acceleration and/or the displacement smoothness, may be determined. The displacement velocity, the displacement acceleration and/or the displacement smoothness may be determined from the mathematical derivatives of the determined displacements. Further, in case the shaft or sleeve comprises a shaft pattern, the shaft pattern may be used for monitoring the tension applied to the shaft or sleeve.

The method may further comprise

1080. Storing data about the determined positions of the medical instrument.

The method may in that case also comprise

1090. Using the data for statistical follow-up.

The stored data may be used for follow-up of training of surgeons. In addition, or as a complement, stored data may be used for quality assurance and/or quality follow-up of minimal invasive intervention, e.g. of training interventions or real-world interventions.

Further modifications of the invention within the scope of the appended claims are feasible. As such, the present invention should not be considered as limited by the embodiments and figures described herein. Rather, the full scope of the invention should be determined by the appended claims, with reference to the description and drawings.

It is to be noted that arrangements corresponding to those disclosed herein may also be utilized for other applications than in an arrangement for minimal invasive intervention, e.g. as a joystick or as an input device for a computer game, an input devices for a vehicle, vessel or aircraft or in a linear sensor.

The invention claimed is:

1. An arrangement for minimal invasive intervention, said arrangement comprising
a rotation body, said rotation body being adapted to receive a medical instrument for minimal invasive intervention, or said rotation body forming a part of a medical instrument, said medical instrument comprising a shaft, at least a portion of a surface of said rotation body comprising a pattern adapted for determining a position of said pattern, said pattern comprising information about position in absolute coordinates, and
a retaining device adapted to at least partly surround said rotation body, such that said rotation body is retained by said retaining device in a manner allowing rotational movement of said rotation body in relation to said retaining device, and
at least one position sensor for determining a position in at least two coordinates of said pattern of said rotation body, said at least one position sensor being located at, in or on said retaining device.

2. The arrangement according to claim 1, wherein said rotation body or said retaining device comprises a hole with an axial direction for receiving said shaft of said medical instrument, said hole allowing an axial displacement of said shaft in said axial direction relative to said rotation body.

3. The arrangement according to claim 1, wherein at least a portion of an outer surface of said rotation body follows a spherical contour or a cylindrical contour.

4. The arrangement according to claim 1 wherein said at least one position sensor and said pattern on said rotation body are adapted for determining said position of said pattern in three coordinates.

5. The arrangement according to claim 1 wherein said pattern is an optical pattern and said at least one position sensor is an optical position sensor.

6. The arrangement according to claim 1, wherein said arrangement further comprises a sensor for determining an axial position of said shaft of said medical instrument.

7. The arrangement according to claim 6, wherein said sensor for determining said axial position is at least partly located inside said rotation body.

8. The arrangement according to claim 6 further comprising a trocar for receiving said shaft of said medical instrument, wherein said sensor for determining an axial position of said shaft of said medical instrument is located in said trocar.

9. The arrangement according to claim 1, further comprising an axial position sensor for determining a position of a shaft pattern being located on a portion of said shaft of said medical instrument.

10. The arrangement according to claim 1, wherein said retaining device provides a bearing for receiving said shaft and allowing said shaft to rotate 3-dimensionally in said bearing, said bearing also allowing axial translation relative to said bearing.

11. A kit comprising an arrangement according to claim 1 and a medical instrument for minimal invasive intervention, said medical instrument comprising a shaft, at least a portion of said shaft comprising a shaft pattern, said shaft pattern being configured to determine rotation of said shaft around its length axis, optionally said shaft pattern being configured to determine rotation of said shaft around its length axis as well as its axial position.

12. The kit according to claim 11 comprising an arrangement wherein said rotation body or said retaining device comprises a hole with an axial direction for receiving said shaft of said medical instrument.

13. The kit according to claim 11, wherein said rotation body forms a sleeve along a portion of said shaft of said medical instrument or constitutes a portion of said shaft.

14. The kit according to claim 13, wherein a portion of said shaft, or sleeve, comprises a shaft pattern for determining a position of said shaft.

15. A system for follow-up of a minimal invasive intervention, said system comprising
an arrangement according to claim 1,
a memory for storing data of determined positions determined by said at least one position sensor.

16. A method for determining a position of a medical instrument by means of an arrangement according to claim 1, said method comprising
determining in at least two coordinates a position of said pattern on said surface of said rotation body by means of said at least one position sensor, said coordinates being absolute,
utilizing said determined position of said pattern to determine said position of said medical instrument.

17. The method according to claim 16 further comprising calibrating the position of a pivot point for said rotational movement of said rotation body in relation to said retaining device, said position of said pivot point being determined in relation to a surrounding environment, such as an operating room and/or a patient.

18. The method according to claim 16, said medical instrument comprising a shaft, said method comprising
determining an axial position of said shaft of said medical instrument,
utilizing said determined position of said pattern and said determined axial position to determine said position of said medical instrument.

19. The method according to claim 16, wherein a portion of said shaft or sleeve comprises a shaft pattern for determining a position of said shaft, wherein the method further comprises
utilizing said shaft pattern on said shaft or sleeve for determining a tension applied to said shaft or sleeve and/or for determining said axial position of the shaft or the sleeve.

* * * * *